US005343860A

United States Patent [19]
Metzger et al.

[11] Patent Number: 5,343,860
[45] Date of Patent: Sep. 6, 1994

[54] ESOPHAGEAL RECORDING/PACING CATHETER WITH THERMISTOR AND CARDIAC IMAGING TRANSCEIVER

[75] Inventors: William T. Metzger, Libertyville; Rimas Buinevicius, Palos Park; Richard M. Bilof, Wonder Lake, all of Ill.

[73] Assignee: Arzco Medical Systems, Inc., Vernon Hills, Ill.

[21] Appl. No.: 973,162

[22] Filed: Nov. 6, 1992

Related U.S. Application Data

[60] Division of Ser. No. 608,200, Nov. 2, 1990, Pat. No. 5,199,433, which is a continuation-in-part of Ser. No. 306,997, Feb. 6, 1989, Pat. No. 5,069,215.

[51] Int. Cl.⁵ .................... A61B 5/0402; A61B 8/12; A61N 1/05
[52] U.S. Cl. ................. 128/642; 128/660.03; 128/662.06; 128/736; 607/124
[58] Field of Search ............... 128/642, 640, 662.06, 128/784, 786, 419 D, 419 P, 660.03, 670, 736; 607/116, 119, 122–125

[56] References Cited

U.S. PATENT DOCUMENTS

| | | |
|---|---|---|
| Re. 31,377 | 9/1983 | Mylrea et al. |
| 3,081,765 | 3/1963 | Kompelien |
| 3,480,003 | 11/1969 | Crites |
| 3,499,435 | 3/1970 | Rockwell et al. |
| 3,533,403 | 10/1970 | Woodson |
| 3,568,660 | 3/1971 | Crites et al. |
| 3,734,094 | 5/1973 | Calinog |
| 3,951,136 | 4/1976 | Wall |
| 4,088,138 | 5/1978 | Diack |
| 4,176,660 | 12/1979 | Mylrea et al. |
| 4,198,963 | 4/1980 | Barkalow |
| 4,304,239 | 12/1981 | Perlin |
| 4,319,580 | 3/1982 | Colley et al. |
| 4,351,330 | 9/1982 | Scarberry |
| 4,442,315 | 4/1984 | Segawa |
| 4,475,555 | 10/1984 | Linder |
| 4,476,872 | 10/1984 | Perlin |
| 4,574,807 | 3/1986 | Hewson |
| 4,640,298 | 2/1987 | Pless et al. |
| 4,658,836 | 4/1987 | Turner |
| 4,660,571 | 4/1987 | Hess |
| 4,683,890 | 8/1987 | Hewson |
| 4,706,681 | 11/1987 | Breyer et al. |
| 4,706,688 | 11/1987 | Don Michael et al. |
| 4,735,206 | 4/1988 | Hewson |
| 4,762,135 | 8/1988 | Puige |
| 4,763,660 | 8/1988 | Kroll et al. |
| 4,765,331 | 8/1988 | Petruzzi |
| 4,817,611 | 4/1989 | Arzbaecher et al. |
| 4,834,102 | 5/1989 | Schwarzchild et al. |
| 4,852,580 | 8/1989 | Wood |
| 4,890,623 | 1/1990 | Cook et al. |
| 4,930,521 | 6/1990 | Metzger |
| 4,960,133 | 10/1990 | Hewson |
| 5,052,390 | 10/1991 | Hewson |
| 5,069,215 | 12/1991 | Jadvar et al. |

FOREIGN PATENT DOCUMENTS

| | | |
|---|---|---|
| 121090 | 2/1972 | Denmark |
| 2003138 | 7/1971 | Fed. Rep. of Germany |
| 133400 | 3/1979 | Fed. Rep. of Germany |
| 2070934 | 2/1981 | United Kingdom |
| 88/3822 | 6/1988 | World Int. Prop. O. |

OTHER PUBLICATIONS

An article entitled "A Pill Electrode For The Study of Cardiac Arrhythmia" by Arzbaecher, published in 1978 in the Journal Medical Instrumentation.
An article entitled "Use of the Pill Electrode For Transesophageal Atrial Pacing" by Jenkins et al. published in the Journal PACE in 1985.

*Primary Examiner*—Lee S. Cohen
*Attorney, Agent, or Firm*—Dressler, Goldsmith, Shore & Milnamow, Ltd.

[57] ABSTRACT

A single use disposable esophageal electrode structure is formed with a planar sheet body member. The body member carries a plurality of spaced-apart conductive electrode members. A temperature sensor can also be carried on the body member. A layer of adhesive on the body member can be used to affix it to an esophageal probe. A plurality of conducting members is coupled to the body member. Each of the conducting members is in turn coupled to a respective one of the electrodes. A free end of the conducting members carries an electrical connector for connection to other electrical units.

23 Claims, 5 Drawing Sheets

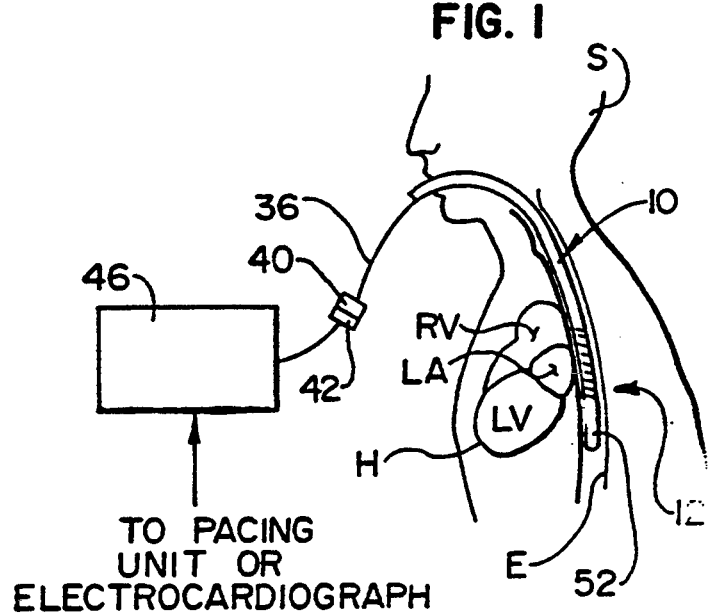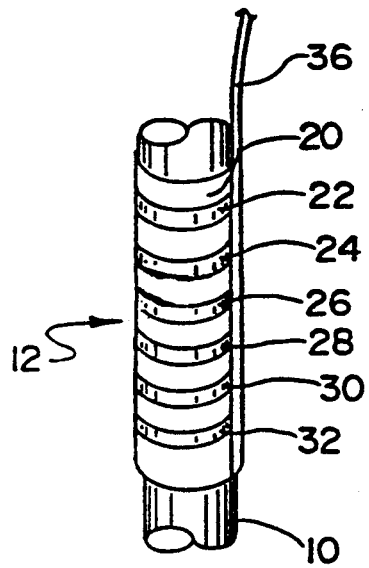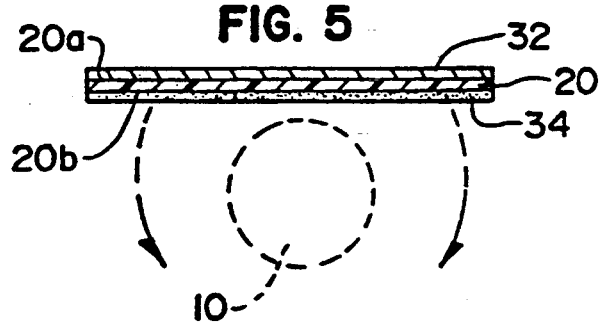

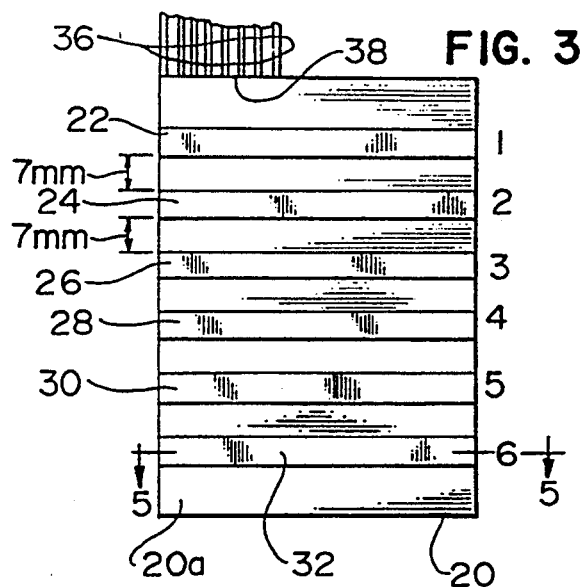
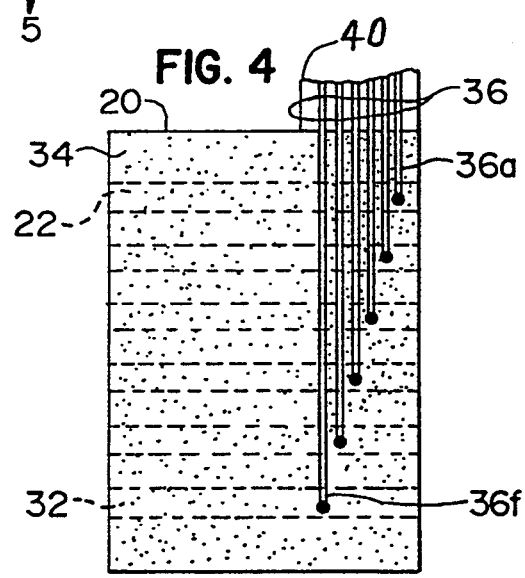
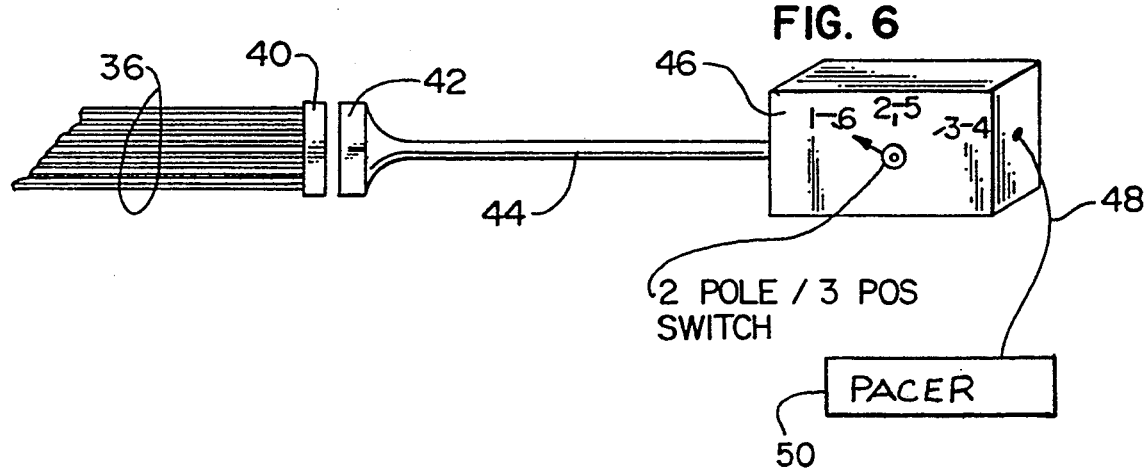

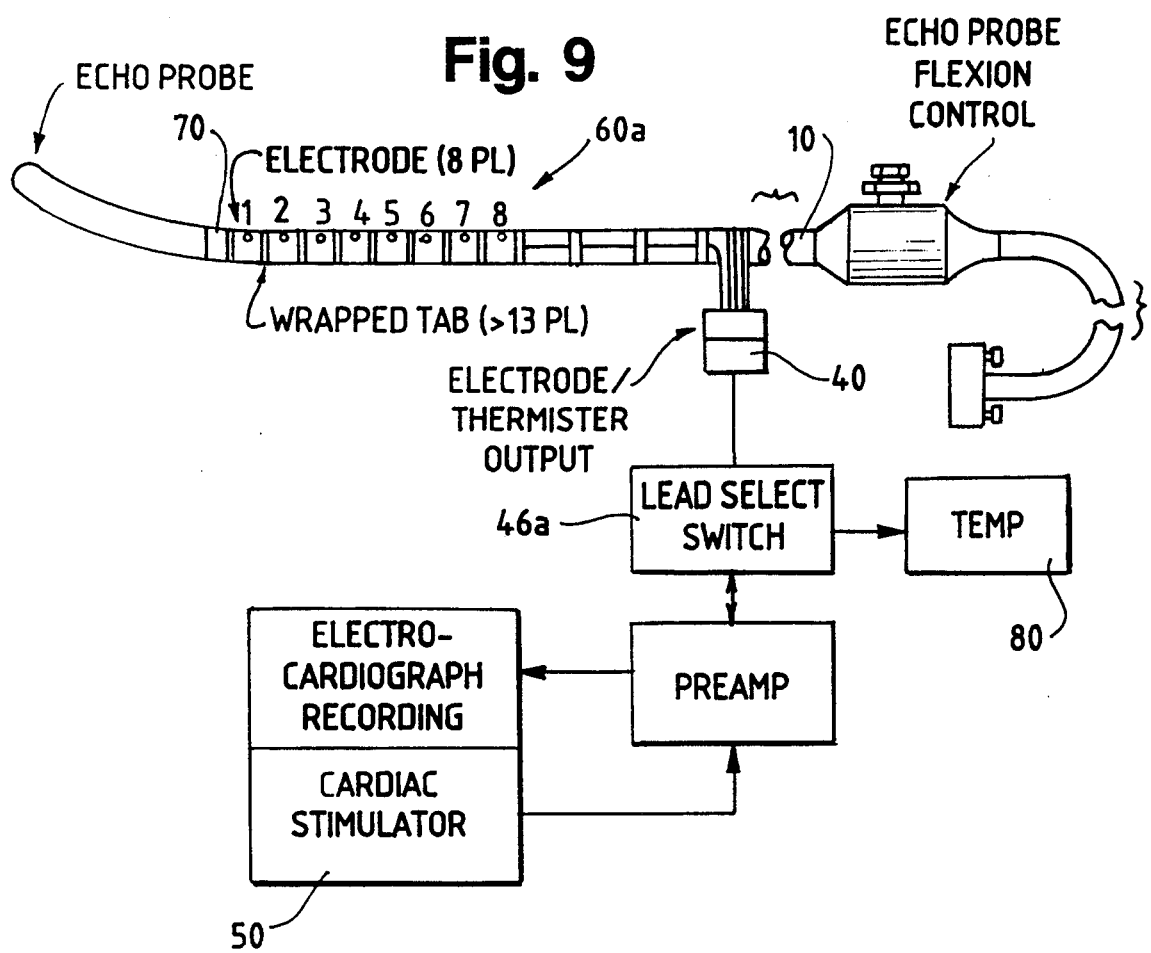
Fig. 9
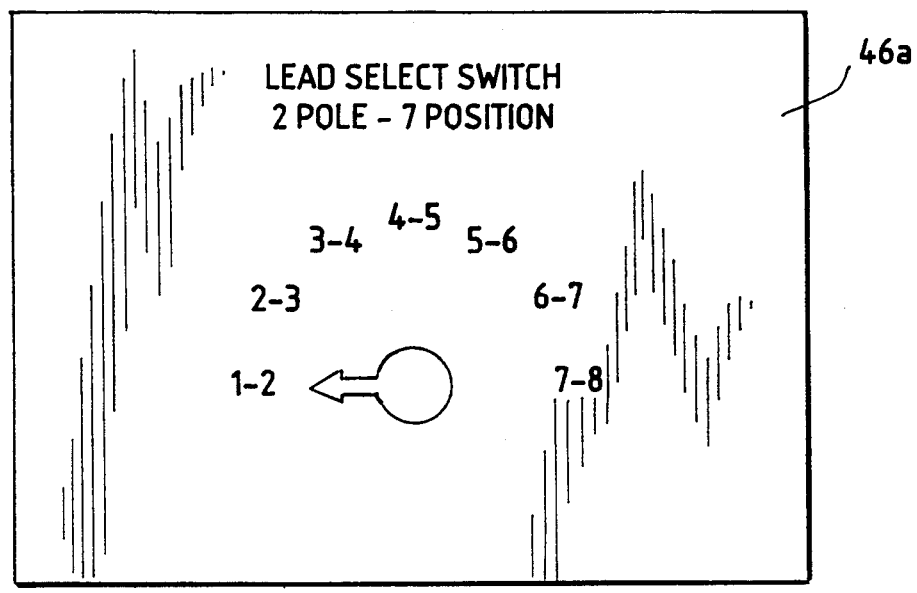

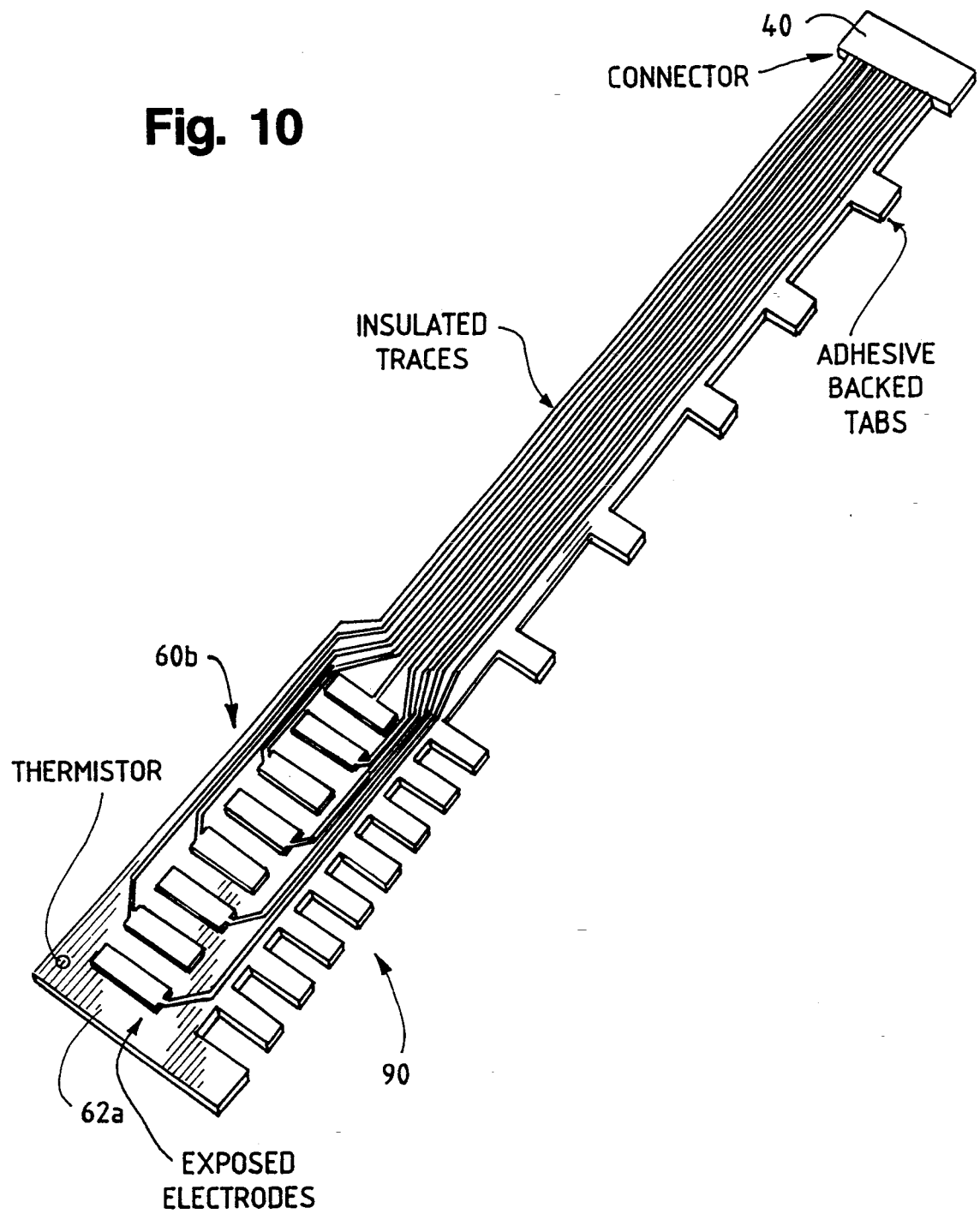

ESOPHAGEAL RECORDING/PACING CATHETER WITH THERMISTOR AND CARDIAC IMAGING TRANSCEIVER This application is a division of application Ser. No. 07/608.200 filed Nov. 2, 1990, now U.S. Pat. No. 5,199,433, which is a continuation-in-part application of Ser. No. 306,997 filed Feb. 6, 1989, now U.S. Pat. No. 5,069,215, and entitled Multiple Electrode Affixable Sheet.

FIELD OF THE INVENTION

The invention pertains to non-invasive cardiac sensing or stimulating. More particularly, the invention pertains to an apparatus and a method for non-invasively recording/pacing a subject's heart while simultaneously performing cardiac imaging.

BACKGROUND OF THE INVENTION

It has been recognized that esophageal electrodes are particularly useful in connection with non-invasive esophageal pacing. One such electrode is disclosed for example in co-pending and commonly assigned U.S. patent application Ser. No. 930,748, now U.S. Pat. No. 4,817,611, entitled Improved Esophageal Electrocardiography Electrode.

It has also been recognized that transesophageal electrocardiography can be used for the purpose of studying myocardial ischemia. One such system is disclosed in commonly assigned and copending U.S. patent application Ser. No. 267,459 entitled Method and Apparatus For Detection of Posterior Ischemia.

It has also been recognized that transesophageal echocardiography can be utilized for the purpose of detecting or evaluating, among other conditions, myocardial ischemia. A particular transesophageal imaging probe is disclosed in U. S. Pat. No. 4,834,102 to Schwarzchild et al. as described in Schwarzchild et al. The transceiver for the imaging probe can be positioned in the esophagus or the stomach of the individual whose heart is being studied.

It would be desirable to be able to combine the pacing capability of esophageal electrodes and the imaging capability of echocardiography probes into a single unit so as to be able to stress the heart and to simultaneously study its characteristics.

SUMMARY OF THE INVENTION

An apparatus and method are provided for esophageal heart pacing and cardiac imaging. The apparatus has a flexible plastic sheet member. The sheet member, which can be generally of a rectangular shape, carries a plurality of spaced-apart electrode members.

A layer of adhesive is carried on the opposite side of the sheet member from the electrodes. Each of the electrodes is connected to one member of a plurality of insulated wires or traces.

The insulated wires can be formed on an elongated mylar sheet member which is affixed at one end to the sheet member. At the other end of the elongated mylar sheet member is an electrical connector which is in turn connected to each of the conductors of the sheet member.

The sheet member can be removably attached to a cardiac imaging probe. As an alternate to a layer of adhesive, other means, such as using a "cling vinyl", can be used to attach the sheet member to the probe.

The electrical connector can in turn be coupled to a switch for selecting various pairs of electrodes. Outputs from or inputs to the selected pair of electrodes can be coupled to or received from an electrocardiograph or an esophageal pacing unit.

Signals from the esophageal pacing unit can be applied to the selected pair of electrodes for the purpose of non-invasively pacing the heart of the subject. Alternately, signals from the selected pair of electrodes can be provided to an amplifier for further processing for the purpose of driving the electrocardiograph.

A temperature sensor, such as a thermistor, is carried on the sheet member. Conductors to/from the temperature sensor are carried on the elongated mylar sheet member.

A method of esophageal cardiac imaging of a subject's heart includes the steps of:
optimally locating a cardiac imaging transmitter in the esophagus;
pacing the heart from an optimal location in the esophagus; and
monitoring the temperature of the subject from the esophagus.

The method can also include steps of recording and selecting an electrode configuration for maximum P wave deflection.

The present esophageal electrode unit is especially advantageous in that it can be manufactured as a single use element which can be affixed to a reusable echocardiography probe prior to use. After use, the electrode unit can be discarded. Alternately, the present multi-electrode/temperature sensor structure could be permanently affixed to an esophageal echocardiography probe.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE FIGURES

FIG. 1 is a partial, side, schematic view of a subject illustrating the relationship between a probe in accordance with the present invention and the heart of the subject;

FIG. 2 is an enlarged portion of a probe carrying a multi-element electrode in accordance with the present invention;

FIG. 3 is an elevational view of one side of a disposable multi-electrode esophageal unit;

FIG. 4 is a second view of the disposable multi-electrode esophageal unit of FIG. 3;

FIG. 5 is a sectional view taken along plane 5—5 of FIG. 1;

FIG. 6 is a pictorial diagram of an electrode selecting switch in accordance with the present invention;

FIG. 9 is an enlarged, side elevational view of an affixable sheet coupled to a block diagram representation of an associated electrical system.

FIG. 10 is a perspective view of yet another embodiment of a disposable multi-electrode esophageal unit.

DETAILED DESCRIPTION OF THE PREFERRED EMBODIMENTS

Figure 7:
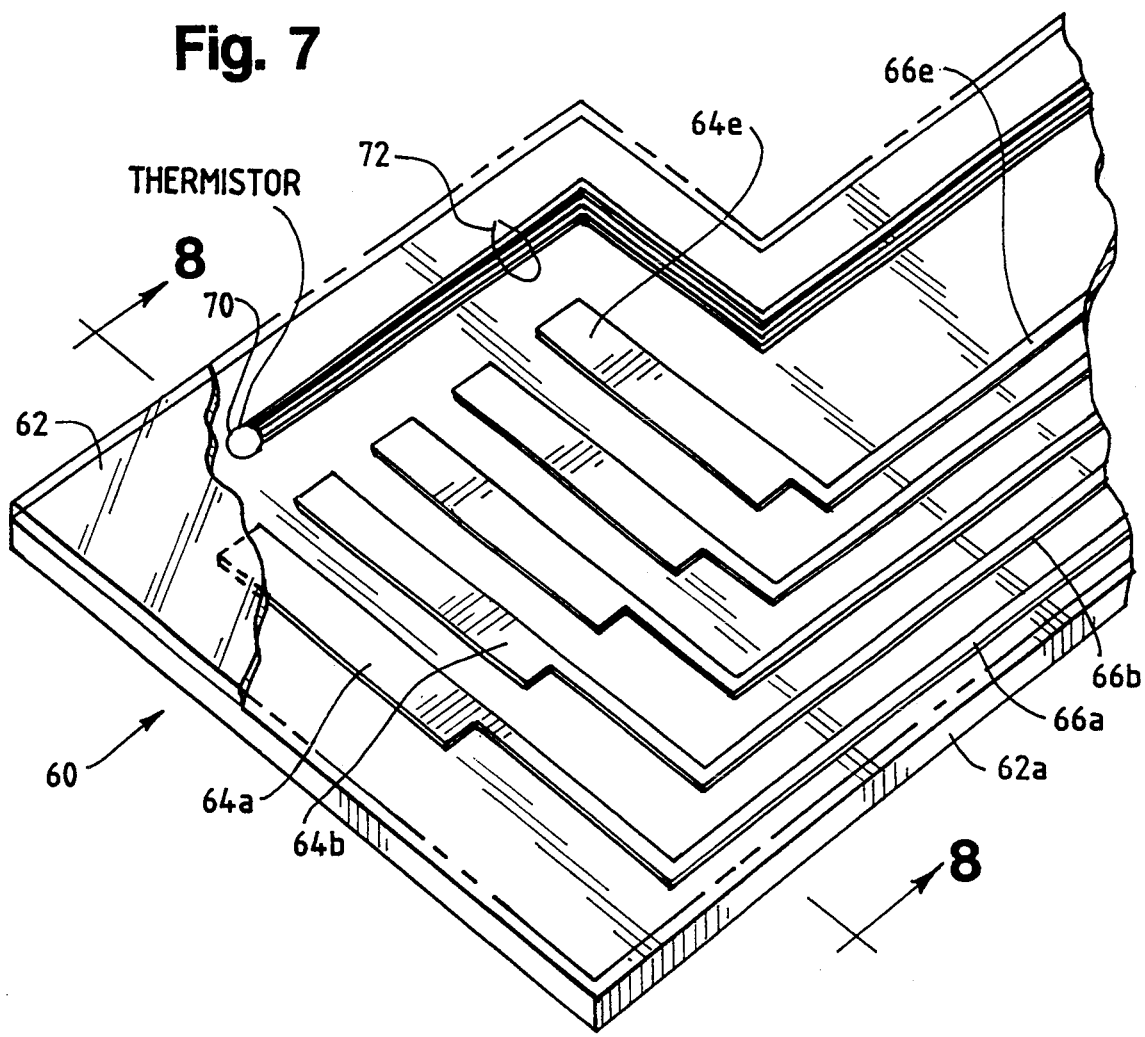
FIG. 7 is an enlarged, fragmentary, perspective view of another affixable sheet in accordance with the present invention.

While this invention is susceptible of embodiment in many different forms, there is shown in the drawing and will be described herein in detail specific embodiments thereof with the understanding that the present disclosure is to be considered as an exemplification of the principles of the invention and is not intended to limit the invention to the specific embodiment illustrated.

FIG. 1 illustrates a subject S having a heart H and an esophagus E with a probe 10 positioned therein. The probe 10 carries a disposable esophageal electrode structure 12. The structure 12 is formed with a flexible medical grade plastic base member 20. The base member 20 carries a plurality of spaced-apart conducting elements 22-32 on a surface 20a.

Each of the elements 22-32 is formed of a bio-compatible conducting material. Each of the elements 22-32 is permanently affixed to the base member 20. The base member 20 on a surface 20b opposite the surface 20a carries a layer of adhesive 34. The layer of adhesive 34 is used to affix the member 20 to the reusable probe 10.

The adhesive layer 34 can be formed of any bio-compatible adhesive with adequate strength so as to fix the electrode structure 12 to the probe 10 for the length of any desired procedure. Subsequent to completion of the desired procedure, the electrode structure 12 is removed from the probe 10 and disposed of. The probe 10 can then be sterilized and reused.

A plurality of conducting members 36 is attached in a region 38 to the member 20. The plurality 36 can be formed with a plastic base member 40 on which is deposited a plurality of spaced apart conducting traces 36a-36f. Each of the traces, such as the trace 36a is electrically connected to a respective one of the conducting members 22-32, such as the member 22.

It will be understood that the details of the formation of the traces 36a-36f and the way in which those traces are carried by the plastic member 40 are not limitations of the present invention. Similarly, the details of how the traces 36a-36f interconnect with the conducting members 22-32 are also not a limitation of the present invention.

A second end of the plurality 36 carries an electrical connector 40 of a conventional variety. The connector 40 can be mated with a corresponding connector 42 which is carried by a multiple conductor cable 44. The cable 44 is in turn coupled to a manually operable switch 46.

The switch 46 could for example be implemented as a two-pole multi-position switch. It will be understood that the exact details of the switch 46 are not a limitation of the present invention. The switch 46 is used to manually select a pair of electrodes from the plurality 22-32. Output from the selected pair of electrodes, or input thereto, on a two-conductor cable 48 can be coupled to an ECG or received from an esophageal pacing unit 50.

The disposable multi-electrode element 12, in combination with the probe 10, makes it possible to combine cardiac pacing as a form of stress simultaneously with echocardiography to determine and sense heart function. For example, if the probe 10 is a commercially available transesophageal ultrasonic probe such as a Hoffrel Instruments, Inc. Model 482 or a Hewlett-Packard Model 21362A.

The electrode structure 12 can be used for pacing the left atrium of the heart H. Simultaneously, an ultrasonic transmitter and receiver 52 on the probe 10 transmits ultrasonic waves toward the heart H and senses ultrasonic reflections therefrom for the purpose of forming an image of the cardiac chambers as the heart H is being simultaneously stimulated.

In a typical procedure, the sheet electrode member 12 is affixed to the parameter of the probe 10 using the layer of adhesive 34. The electrode structure 12 is located at a level about 10 centimeters above the ultrasonic transmitter and receiver 52 in the probe.

The ultrasonic transmitter/receiver 52 is carried at a distal end of the probe 10. The multi-electrode element 12 is carried on the probe 10 adjacent the transmitter/receiver 52 but spaced therefrom toward the proximal end of the probe 10.

The probe 10 is inserted in a conventional fashion into the esophagus E of the subject S. The transmitter-receiver 52 is then positioned in the esophagus E optimally located to carry out the cardiac imaging function.

With the transmitter-receiver 52 optimally positioned, the optimal electrode or electrodes from the plurality 22-32 can be selected using the switch 46. Since the plurality of electrodes 22-32 is carried on the catheter 10, displaced away from the transmitter-receiver 52 toward the proximal end or connector 40, one or more of the members of the plurality will be optimally located adjacent the posterior surface of the heart H to carry out the desired recording and/or pacing function. A pacing unit, coupled to the cable 48, can then be used for pacing the heart H simultaneously with carrying out a cardiac imaging function.

By way of example and not by way of limitation, the width of each of the electrode members 22-32 can be on the order of 5 or 7 millimeters with a corresponding spacing of 2.0-2.5 centimeters. The length dimension of the sheet member 20 can be in a range of 5-20 centimeters and the width dimension can be on the order of 40 millimeters.

The length of the plastic extension member 40, which could be formed of mylar or vinyl can be on the order of 50-60 centimeters. The body member 20 can also be formed of a mylar or vinyl sheet. It will be understood that any medical grade plastic could be used for the body member 20 without departing from the spirit and scope of the present invention.

Further, in a typical installation the switching unit 46 can be connected so as to switch as electrode pairs, electrodes 22, 32; 24, 30; or 24, 26. If desired, other pairs of electrodes could be switched such as, 22, 24; 24, 26; 26, 28; 28, 30; or 30, 32. If desired, additional electrodes can be formed in base member 20.

Alternately, the multiple electrode system 12 can be fabricated permanently attached to an imaging probe. Imaging probes, of the type discussed above, usually include an ultrasonic transmitter and receiver located at the end of the probe.

The transmitter is located in the esophagus below the heart and is oriented on the probe to transmit toward the heart. Reflected ultrasonic waves are detected by the transceiver, converted to corresponding electrical signals and transmitted from the probe to outside analysis circuitry.

Hence, it will be understood that the multiple electrodes 22-32 could be permanently attached to the body of the esophageal ultrasonic probe as generally indicated in FIG. 1.

Figure 8:
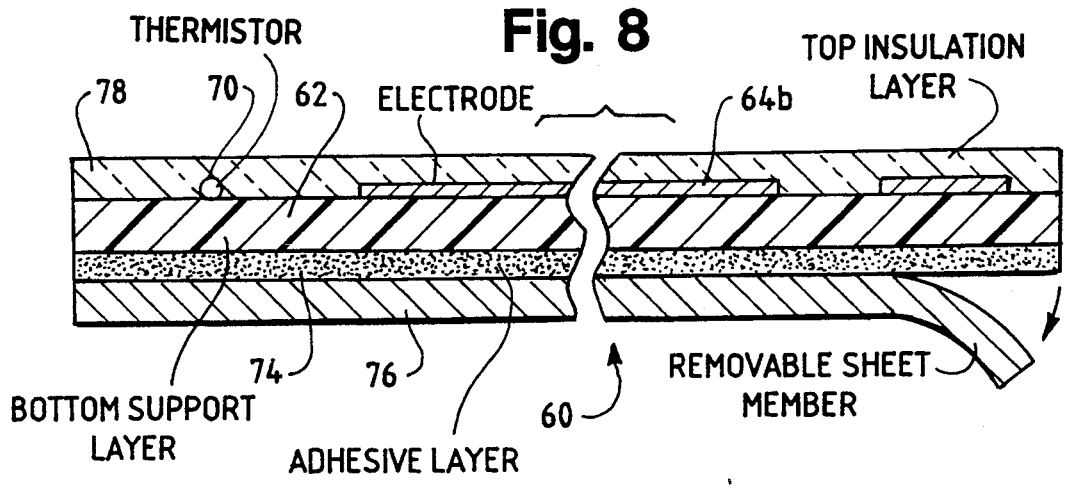
FIG. 8 is a sectional view taken along plane 8—8 of FIG. 7.

FIG. 7 and 8 illustrate an alternate single use disposable sheet electrode structure 60. The structure 60 includes a flexible, generally rectangular, planar plastic base member 62. Formed on the base member 62 is a plurality of spaced apart metal electrodes 64a-64e.

Each of the electrodes 64a-64e is coupled to an elongated conducting member, such as the respective members 66a-66e. The elongated conducting men, hers 66a-66e are carried in part on the planar member 62 and in part on an extension 62a thereof. The elongated conducting members 66a-66e can be terminated at a connector, such as the connector 40 at a proximal end of the probe 10.

Also carried on the sheet member 62 is a temperature sensor 70. The temperature sensor 70 can be, for example, a thermistor. Elongated flexible conductors 72 carried in part on the sheet member 62 and in part on the sheet member extension 62a extend from the thermistor or temperature sensor 70 to the proximal end connector 40.

As illustrated in FIG. 8, the planar sheet member 62 carries on one side thereof a layer of adhesive 74. The structure 60 is removably attachable to the echocardiography probe 10 using the adhesive layer 74.

Alternately, the base member 62 can be formed of a so-called "clear cling vinyl" material from Flexcon.

The layer of adhesive 74 can be protected prior to use by a removable paper sheet member 76. A planar, top insulating member 78, formed of a flexible planar plastic overlies the base member 62 and isolates the thermistor 70 as well as portions of the conductor 64a-64e along with the conductors 66a-66e and 72 from the patient.

The removable sheet member 60 can be removably affixed to a transesophageal imaging probe, such as the probe 10 previously discussed. The sheet member 60 is affixed to the probe 10 displaced from the distal end imaging transceiver 52 toward the proximal end of the probe 10.

When the probe 10, carrying the sheet member 60, is positioned in the esophagus E of the patient, the location of the transmitter 52 can be optimally set for carrying out the imaging function. Then, one or more of the members of the plurality of electrodes 64a-64e can be recording and/or selected for optimally carrying out an esophageal cardiac pacing function simultaneously with carrying out the imaging function. Further, at the same time the core temperature of the individual can be continuously monitored using the thermistor 70.

FIG. 9 illustrates a unit 60a, coupled to the echocardiography probe 10, electrically connected via the eight connector 40 to an electrode selector switch 46a and pacing unit 50. In addition, the thermistor 70 is coupled via the connector 40 and the switch 46 to a temperature sensor module 80 which for example could provide a digital display of the individual's temperature.

Without limitation and for example only the base member 62 could be formed of a vinyl plastic with a size on the order of 1 inch wide by 16 to 20 inches long. The indicated electrode members corresponding to the electrodes 64a-64e could be formed of deposited stainless steel. Silver conductive ink can be used to form the conductors 66a-66e and 72. Alternately, conducting foil or film can be applied to the base member to form the conductors.

The size of the exposed dimensions of electrodes can be on the order of 0.16 inches by 0.60 inches. It will be understood that while five electrodes 64a-64e have been disclosed in FIG. 7 and eight have been disclosed in FIG. 9, the exact number of electrodes is not a limitation of the present invention.

The electrode structure 60 can be permanently affixed to the probe 10. Alternately, in connection with a removably attachable form of the structure 60 the way in which the attachment is carried out is not a limitation of the present invention. Instead of the disclosed layer of adhesive, a vinyl plastic body member which will readily "cling" to the probe 10 can be used. Mechanical means of attachment could also be used.

FIG. 10 illustrates an alternate electrode structure 60b. The structure 60b includes a plurality of adhesive backed tabs 90. The tabs 90 removably attach the structure 60b to an echo probe 10 by attaching to a portion of a sheet member 62a.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A disposable esophageal pacing and monitoring member usable with an esophageal cardiac imaging probe comprising:
   a flexible, planar sheet member;
   a layer of adhesive carried on said sheet member;
   a removable protective cover overlying said adhesive layer;
   a plurality of spaced apart planar electrodes carried on said sheet member; and
   a temperature sensor carried on said sheet member.

2. A monitoring member as in claim 1 including a second planar sheet member that overlies, at least in part, said planar electrodes.

3. A monitoring member as in claim 1 including a plurality of elongated, flexible, conducting members with some members of said plurality coupled to corresponding members of said plurality of electrodes with other members of said plurality coupled to said temperature sensor.

4. A disposable esophageal pacing and monitoring member usable with an esophageal cardiac imaging probe comprising:
   a flexible, planar sheet member;
   a plurality of adhesive backed tabs carried on said sheet member;
   a plurality of spaced apart planar electrodes carried on said sheet member; and
   a temperature sensor carried on said sheet member with said tabs usable to removably affix said sheet member to the probe.

5. A disposable esophageal member usable with an esophageal cardiac imaging probe comprising:
   a flexible, planar sheet member;
   a plurality of adhesive backed tabs carried on said sheet member;
   a plurality of spaced part planar cardiac stimulating conductive members carried on said sheet member; and
   a temperature sensor carried on said sheet member with said tabs usable to removably affix said sheet member to the probe.

6. A member as in claim 5 including a second planar sheet member that overlies, at least in part, said planar stimulating members.

7. A disposable device that is attachable to an esophageal probe comprising:

a flexible sheet member;

attaching means on said sheet member for attaching said sheet member to the esophageal probe;

a temperature sensor on said sheet member and an electrode carried on said sheet member.

8. A disposable device that is attachable to an esophageal probe comprising:

a flexible sheet member;

attaching means on said sheet member for attaching said sheet member to the esophageal probe;

a temperature sensor on said sheet member and a plurality of electrodes carried on said sheet member.

9. A device in accordance with claim 8 including a second planar sheet member that overlies, at least in part, said electrodes.

10. A device in accordance with claim 8 including a plurality of elongated, flexible conducting members wherein members of said plurality are coupled to respective members of said plurality of electrodes.

11. A device in accordance with claim 10 including an electrical connector attached to said elongated conducting members at a location displaced from said sheet member.

12. A device in accordance with claim 11 including a selector means for selecting at least one of said electrodes, said selector means being couplable to said connector.

13. A device insertable into an esophagus comprising:

a flexible, planar elongated sheet member;

a plurality of adhesive backed tabs carried on said sheet member;

a plurality of spaced apart planar electrodes carried on said sheet member; and a temperature sensor carried on said sheet member.

14. A multi-element electrode structure affixable to an essentially cylindrical esophageal probe which can then be inserted into the esophagus of a patient, the electrode structure comprising:

a rectangular insulative sheet member having a selected length dimension and a width dimension corresponding to the perimeter of the esophageal probe;

a plurality of spaced electrodes carried by said sheet member;

adhesive means carried by said sheet member for affixing said member to the probe;

a plurality of elongated conducting members with each said conducting member having an end in electrical contact with a respective one of said electrodes; and a temperature sensor carried on said sheet member.

15. A multi-element electrode in accordance with claim 14 including an electrical connector displaced from said sheet member, said electrical connector being carried by said plurality of elongated conducting members.

16. A multi-element electrode in accordance with claim 15 including means, couplable to said connector, for electrically selecting at least one of said electrodes.

17. A multi-element electrode in accordance with claim 15 including means for electrically selecting at least first and second of said electrodes.

18. A multi-element electrode in accordance with claim 14 including a selector means for selecting at least one of said electrodes.

19. A multi-element electrode structure affixable to an essentially cylindrical esophageal probe which can then be inserted into the esophagus of a patient, the electrode structure comprising:

a rectangular insulative sheet member having a selected length dimension and a selected width dimension, said sheet member being wrappable on the esophageal probe;

means, carried by said sheet member, for affixing said member to the probe;

a plurality of spaced, conducting electrode members carried by said sheet member;

a plurality of elongated conducting members, each of said conducting members having an end in electrical contact with a respective one of said electrode members; and a temperature sensor carried on said sheet member.

20. A multi-element structure in accordance with claim 19 wherein each of said plurality of elongated conducting members carries an electrical connector displaced from said sheet member.

21. A multi-element electrode structure in accordance with claim 19 including means, couplable to said connector, for electrically selecting at least one of said electrode members.

22. A multi-element electrode structure in accordance with claim 19 including means for electrically selecting at least first and second of said electrode members.

23. A multi-element electrode structure affixable to an essentially cylindrical esophageal probe which can then be inserted into an esophagus of a patient, the electrode structure comprising:

an insulative sheet member;

a plurality of spaced electrodes carried by said sheet member;

means for affixing said sheet member to the probe such that at least some of said electrodes substantially encircle said probe;

a plurality of elongated conducting members, each of said conducting members having an end in electrical contact with a respective one of said electrodes; and a temperature sensor carried by said sheet member.

* * * * *